United States Patent [19]
Bandurco et al.

[11] Patent Number: 4,639,518
[45] Date of Patent: Jan. 27, 1987

[54] SUBSTITUTED QUINAZOLINEDIONES

[75] Inventors: Victor T. Bandurco, Bridgewater, N.J.; Stanley C. Bell, Narberth, Pa.; Donald W. Combs, Piscataway; Robert Falotico, Belle Mead, both of N.J.; Alfonso J. Tobia, Doylestown, Pa.

[73] Assignee: Ortho Pharmaceutical Corporation, Raritan, N.J.

[21] Appl. No.: 653,620

[22] Filed: Sep. 24, 1984

[51] Int. Cl.[4] .............................. C07D 239/96
[52] U.S. Cl. .................................. 544/285; 544/116; 544/251; 549/436; 558/52; 558/48; 560/23; 560/39; 562/434; 562/458; 568/442
[58] Field of Search ........................................ 544/285

[56] References Cited

U.S. PATENT DOCUMENTS

| | | | |
|---|---|---|---|
| 3,983,120 | 9/1976 | Beverung et al. | 544/286 |
| 3,988,340 | 10/1976 | Partyka et al. | 544/286 |
| 4,146,717 | 3/1979 | Yamamoto et al. | 544/286 |
| 4,202,895 | 5/1980 | Inaba et al. | 544/286 |

*Primary Examiner*—Glennon H. Hollrah
*Assistant Examiner*—James H. Turnipseed
*Attorney, Agent, or Firm*—Benjamin F. Lambert

[57] ABSTRACT

The synthesis of 5,6-dioxy substituted quinazolinediones is described. The novel quinazolinediones are useful as cardiotonic agents.

8 Claims, No Drawings

SUBSTITUTED QUINAZOLINEDIONES

The present invention relates to substituted quinazolinediones having the following general formula:

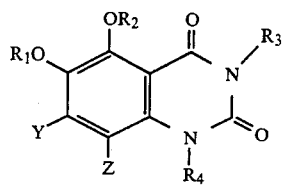

wherein $R_1$ and $R_2$ are the same or different substituents and are hydrogen, lower alkyl having 1-5 carbon atoms or when taken together form a methylenedioxy group; Y and Z are the same or different and are hydrogen, nitro, amino, acetamido, alkylamino wherein the alkyl group has 1-5 carbon atoms, alkyl having 1-5 carbon atoms, cycloalkylamino and cycloalkyldiamino wherein the cycloalkyl group has 4-8 carbon atoms, carboxy, carboalkoxy wherein the alkoxy group has 1-5 carbon atoms, cyano, methanesulfonyl, carboxamido, halo including bromo, chloro, fluoro and iodo; $R_3$ is hydrogen, alkyl having 1-5 carbon atoms, amino, hydroxyalkyl, dialkylamino, dialkylamino alkyl, and haloalkyl wherein the halogen is bromo, chloro or fluoro and the alkyl group in each case contains 1-5 carbon atoms, cycloalkylamino and cycloalkylaminoalkyl wherein the cycloalkyl group contains 5-6 carbon atoms and the alkyl group 1-5 carbon atoms, phenyl and substituted phenyl, for example, halophenyl such as p-chlorophenyl, p-fluorophenyl, o-chlorophenyl, lower alkoxyphenyl and diloweralkoxy phenyl such as methoxy and ethoxy phenyl, alkylphenyl wherein the alkyl group contains 1-5 carbon atoms, substituted alkylphenyl wherein the substituent is a nitro, amino, alkylamino, cycloalkylamino, cyclodialkylamino, carboxy, carboalkoxy, mono- and dihydroxy, cyano, methanesulfonyl, carboxamido, or halo group; provided that when $R_3$ is amino or alkylamino Y and Z are not hydrogen at the same time; $R_4$ is hydrogen,

wherein $R_5$ is hydrogen, lower alkyl having 1-5 carbon atoms; X is carboxy, carboalkoxy wherein the alkoxy group has 1-3 carbon atoms, cyano, carboxamido, methanesulfonyl, formyl, benzoyl, substituted benzoyl wherein the substituent is an alkyl group having 1-4 carbon atoms, and the pharmaceutically acceptable salts of the quinazolinediones.

Certain quinazolinediones have been reported in the literature. In U.S. Pat. No. 4,287,340 quinazolinediones having a halo substituent at the 6-position and an alkoxy substituent at the 7,8-positions with no substitution in the 1-position have been reported. These compounds were used in the synthesis of 2,4-diamino quinazolines and were useful as antihypertensive agents. Quinazolinediones having a halo substituent in the 8-position and an alkoxy group in the 6,7-positions with no substitution in the 1-position have also been reported. [W. Armarego and P. Reece, Aust. J. Chem. (1981), 34, 1561]. In addition, quinazolinediones have been reported in U.S. Pat. Nos. 4,405,623, 4,268,511 and 4,335,127; Belgium Pat. No. 803800 and Dutch Pat. No. 7407910. None of the compounds described in these publications is active as a cardiotonic agent. In addition, quinazolinediones having substitution in the 5,6-positions have not been reported in the literature.

The novel 5,6-dioxy substituted quinazolinediones can be synthesized according to the following diagram:

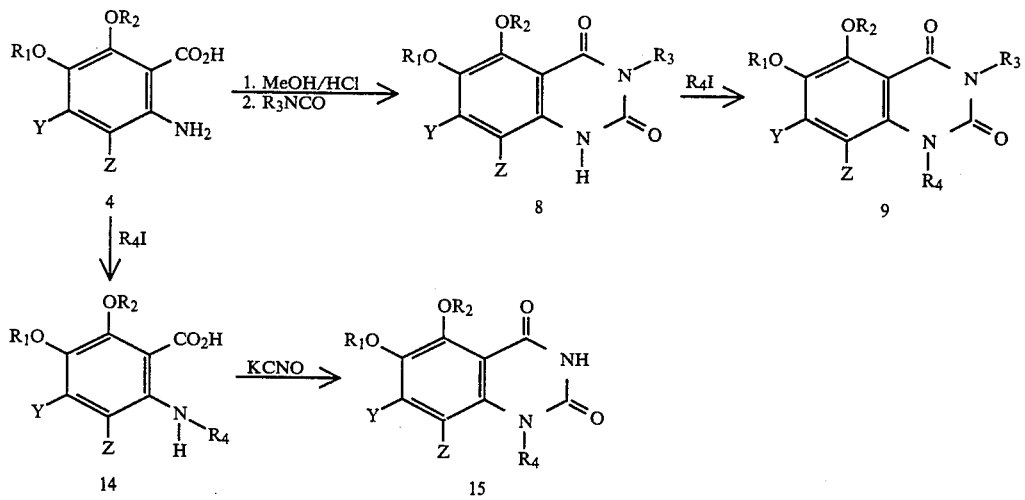

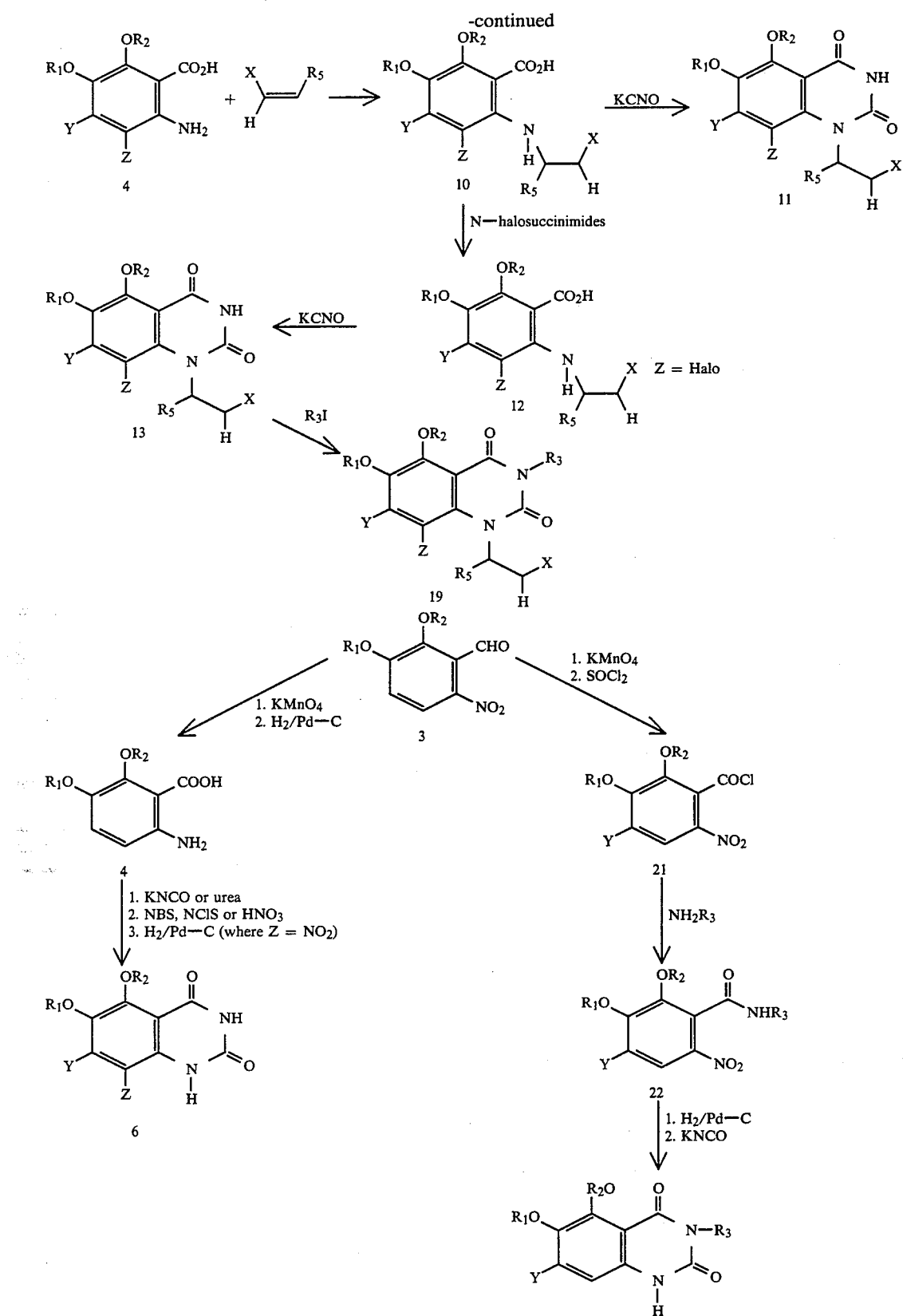

wherein Y = H, Z = Br, Cl, NO₂, NH₂

The 5,6-dioxy substituted quinazolinediones wherein R₄ is hydrogen (6) are prepared by reacting an appropriately substituted nitro benzaldehyde with an oxidizing agent, such as, for example, sodium perchlorate, potassium permanganate or chromium trioxide in a suitable solvent such as acetone, chloroform or dichloromethane to form the corresponding nitro benzoic acid which is then reduced with a reducing agent such as hydrogen on Pd/C to the corresponding amine. The substituted amino benzoic acid is then fused with urea or urethane or reacted with an alkali metal cyanate, such as potassium or sodium cyanate to form the dialkoxy quinazolinedione (6). Those compounds wherein $R_4$ is

are prepared by first reacting an appropriately substituted amino benzoic acid (4) with an olefinic acid or olefinic ester such as acrylic acid or methyl acrylate in a suitable solvent such as acetic acid. The adduct (10) which forms is then reacted with an alkali metal cyanate to form the corresponding quinazolinedione (11).

The quinazolinediones wherein Y and/or Z are halo are prepared from quinazolinediones 6 by halogenation. Halogenating agents which can be employed include chlorine, bromine, sulfuryl chloride, N-halosuccinimides such as N-chlorosuccinimide, sodium or calcium, hypochloride and sodium hypobromite.

The N-3 and N-1 substituted quinazolinediones 8 and 15 are prepared by reacting the substituted 2-aminobenzoic acids, 4 and 14, with the appropriate isocyanates. Alternatively, the N-3 substituted quinazolinediones 8 can be prepared by fusion of the intermediate urethane with an amine, $R_3NH_2$. Alternatively, the nitrobenzoic acid compound is converted to the acid halide (21) by reaction with, for example, thionyl chloride. Reaction of the acid halide (21) with the appropriately substituted amine ($R_3NH_2$) gives the nitro amide (22). Reduction of the nitro amide (22) with a reducing agent such as hydrogen and Pd/C and cyclization with an cyanate such as potassium cyanate in a suitable solvent such as, for example, acetic acid, or with an alkyl haloformate such as ethyl chloroformate gives the N-3 substituted quinazolinedione (23).

The N- substituted 2-aminobenzoic acid intermediates, 10, are prepared by reacting a substituted 2-aminobenzoic acid 4 with an appropriately substituted olefin, such as methyl cinnamate, methyl acrylate, methyl crotonate, acrylonitrile, acrylic acid and methyl methacrylate, for example. The reaction is generally carried out in the presence of a basic catalyst such as sodium carbonate, sodium methoxide, or quarternary ammonium hydroxides such as benzyltrimethylammonium hydroxide. No catalyst is necessary, however, when the reaction is carried out using acetic acid as the solvent.

The N-1 substituted quinazolinediones 11 are then prepared by treatment of 10 with potassium cyanate. Alternatively, quinazolinediones 11 can be prepared directly from the 2-aminobenzoic acids 4 without isolating the N-1 substituted 2-aminobenzoic acid, 10. Treatment of mono N-substituted quinazolinediones 8 with either alkyl iodides such as methyl iodide, for example, or a dialkyl sulfate such as dimethyl sulfate, for example, results in a di N-1,3 substituted quinazolinedione.

Hydrolysis of dialkoxy quinazolinediones 6 with hydrobromic or hydriodic acid furnishes the corresponding dihydroxy analogs.

Intermediates 3 and 4 in the synthesis where $R_1=R_2=CH_3$ and $Y=Z=H$ are known compounds. [J. Med. Chem. 25, 703 (1982)]

The compounds having other alkyl substituents can be prepared in an analogous fashion by starting with the appropriately substituted starting materials (1). In those cases where the appropriately substituted analogs of 1 are not available, the desired Y and Z substituents can be introduced when the 2-aminobenzoic acids (4) are treated with the appropriate reagents to obtain those compounds wherein $R_1$, $R_2$, $R_3$, $R_4$, $R_5$, X, Y and Z are as defined above. For example, the nitro compounds can be 10 prepared by nitrating compound 4 with an appropriate nitrating agent such as nitric acid. The corresponding amino compounds are then obtained by reduction of the nitro group.

The novel quinazolinediones of this invention are active cardiotonic agents. In addition, some of the compounds are active renal vasodilators.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain per dosage unit, e.g., tablet, capsule, powder, injection, teaspoonful and the like, from about 1 to about 200 mg/kg and preferably from about 0.5 to about 50 mg/kg of the active ingredient.

The following examples describe the invention in greater particularity and are intended to be a way of illustrating but not limiting the invention.

EXAMPLE 1

2-Benzenesulfonyloxy-3-methoxybenzaldehyde o-Vanillin (350 g, 2.3 mols) was added to a solution of NaOH (166 g, 4.15 mols) in 2 l water. Benzenesulfonyl chloride (485 g, 2.74 mols) was added to the slurry at 20°–25° C. over 1 hour. The solid which formed was collected on a filter, washed with 2 l water, and redissolved in $CH_2Cl_2$. That solution was dried ($MgSO_4$) and evaporated to a slurry. The solid was collected on a filter, the filtrate was further evaporated and filtered. The solid was washed with MeOH and dried in vacuo to afford the desired product, (511 g, 81.4%), mp 120°–122° C.

EXAMPLE 2

2-Benzenesulfonyloxy-3-methoxy-6-nitrobenzaldehyde 2-Benzenesulfonyl-3-methoxybenzaldehyde (250 g, 0.85 mols) was added to 90% HNO₃ (2250 ml) with stirring at −2° C. over 10 minutes then stirred 5 minutes and poured over 8 kg of crushed ice. The solid which precipitated was filtered and washed with water. Both the solid and filtrate were extracted with CH$_2$Cl$_2$, the extracts were washed with aqueous K$_2$CO$_3$, dried (MgSO$_4$) and evaporated with addition of MeOH to displace the CH$_2$Cl$_2$ to 400 ml, cooled, filtered and the solid washed with MeOH and dried in vacuo to afford (188 g, 65%) of aldehyde, mp 152°–155° C., NMR CDCl$_3$(TMS) d 3.73 (s, 3H, OCH$_3$), d 7.1 −8.20 (m, 9 H, Ar H), 10.13) (s, 1H, CHO).

EXAMPLE 3

2-Benzenesulfonyloxy-3-methoxy-4-nitrobenzaldehyde

The filtrate from the above reaction contained the product of Example 3. Crystallization from methanol afforded 20% of the 4-nitrobenzaldehyde, mp 74°–76° C.

EXAMPLE 4

2-Hydroxy-3-methoxy-6-nitrobenzaldehyde

2-Benzenesulfonyloxy-3-methoxy-6-nitrobenzaldehyde (115 g, 0.39 mols) was dissolved in 6 l MeOH and refluxed while a solution of KOH (68 g, 1 mol) in 145 ml H$_2$O was added. The thick slurry was cooled to 30° C. and filtered. The collected solid was suspended in 1.5 l water and acidified with concentrated HCl (150 ml). The slurry was extracted with CH$_2$Cl$_2$, the extracts were dried (MgSO$_4$) and evaporated. The resulting solid was dissolved in MeOH (1.2 l) and evaporated to 500 ml. The crystals which formed were filtered and washed with MeOH to afford desired aldehyde, (20 g) mp 100°–101° C., IR, KBr 6.08 mu CHO; NMR, CDCl$_3$(TMS), 4.00 (s, 3H, OCH$_3$), 7.03, 7.72 (each d, J=9, each 1H, 4,5 H), 10.48 (s, 1H, OH), 12.45 (s, 1H, CHO).

EXAMPLE 5

2-Hydroxy-3-methoxy-6-nitrobenzaldehyde potassium salt

Nitro benzenesulfonate from Example 4 (200 g) was dispersed in methanol (8 l) and heated to 60° C. A solution of KOH (127 g) in water (270 ml) was added over 30–60 minutes. The slurry was refluxed for 1 hour, cooled to 25°–30° filtered, and the solid washed with MeOH (1 l). The orange solid was dried in the vacuum oven to afford (132 g, 95%) of the desired product.

EXAMPLE 6

2,3-Dimethoxy-6-nitrobenzaldehyde

Potassium salt from Example 5 (396 g) was slurried with DMF (8 l) and added to a 1 l flask containing 800 g potassium carbonate. Dimethyl sulfate (420 ml) was added in portions at 60° over 1 hour and the reaction was stirred at 60° overnight. The K$_2$CO$_3$ was washed with acetone and the washings were added to the distillation residue and again solvent was removed in vacuo. The dry residue was treated with water (1 l) and extracted with CH$_2$Cl$_2$. The extracts were dried, evaporated, and the product was crystallized from methanol to afford the product, (335 g, 94%) mp 109°–111° C.

EXAMPLE 7

2,3-Dimethoxy-6-nitrobenzoic Acid 2,3-Dimethoxy-6-nitrobenzaldehyde from Example 6 (331 g) was added to acetone (2.5 l) in a 12 l flask. A saturated solution (approximately 60–65 g/ l) of potassium permanganate was added until TLC showed no starting material. Approximately 7 l was required. The reaction mixture was filtered to remove the MnO$_2$ and was washed with 2.5N KOH and acetone (2 l each). The combined filtrates were evaporated to dryness and acidified with concentrated HCl. The precipitated solid was collected on a filter, washed with water (250 ml) and dried overnight. The solid was dissolved in 2 l acetone, treated with MgSO$_4$ and charcoal, evaporated to 500 ml and cooled to 5°. The crystals were filtered, washed with acetone and hexane and dried to afford dimethoxy acid (234 g, 65.7%) mp 187°–189° C.

EXAMPLE 8

2-Amino-5,6-dimethoxybenzoic Acid

A slurry of 2,3-dimethoxy-6-nitrobenzoic acid (5 g, 22 mM) in EtOH (200 ml) was treated with Pd/C (5%, 0.5 g) and the mixture hydrogenated on a Parr apparatus at 45 psi for 1 hour. The reaction mixture was filtered and the solvent removed from the filtrate. An off-white semi-solid residue was isolated. Crystallization from isopropanol afforded the amine, 3.8 g (86.7%), mp 71°–72° C.

EXAMPLE 9

2-Benzenesulfonyloxy-3-methoxy-4-aminobenzaldehyde

The 4-nitrobenzaldehyde from Example 3 (82.0 g, 243 mM) in glacial acetic acid (323 ml) and H$_2$O (332 ml) at 90°–95° C. was treated with iron powder (103 g, 40 mesh) added in 10–12 portions during ¾ hour with vigorous stirring. When addition was complete the suspension was heated at 90°–95° C. for 3 hours. The reaction mixture was cooled and H$_2$O (380 ml) added. The mixture is then filtered and the dark brown solid washed with EtOAc. Removal of solvent afforded 50 g of crude product. Crystallization from EtOAc and treatment with charcoal afforded a yellow solid, 50 g (67%), mp 280°–282° C. dec.

EXAMPLE 10

5,6-Dimethoxyquinazolin-2,4(1H, 3H)-dione

2-Amino-5,6-dimethoxybenzoic acid (10.5 g, 53.2 mM) was dissolved in glacial acetic acid (100 ml) and potassium cyanate (10.8 g, 133.0 mM) in 120 ml H$_2$O was added gradually and stirred for 2 hours at 60° C. After cooling the reaction mixture to 20° C., sodium hydroxide pellets (78.2 g, 196 mole) were added while maintaining the temperature below 60° C. The reaction mixture was then heated at 90° C. for 45 minutes. Upon cooling in an ice bath, the sodium salt of the product precipitated, was filtered resuspended in H$_2$O (120 ml), acidified (pH 3) with concentrated HCl, cooled, and filtered to give the crude product. Trituration with warm isopropanol afforded (60.8%) of a white solid, mp 266°–268° C.

EXAMPLE 11

5,6-Dimethoxy-8-choroquinazolin-2,4(1H, 3H)-dione

A slurry of 5,6-dimethoxyquinazoline-2,4(1H, 3H)-dione (4.0 g, 18 mM) in CHCl$_3$ (1000 ml) was treated with N-chlorosuccinimide (4.6 g, 34.4 mM). The mixture was then refluxed with stirring for 18 hours. A light brown clear solution formed. It was cooled and subsequently washed with 10% aqueous sodium thiosulfate. The organic fraction was dried (anhyd. MgSO$_4$), filtered and the solvent removed in vacuo to give a brown solid. Trituration with isopropanol followed by warm methanol afforded the product as a light brownish solid; 2.4 g (52.2%); mp 282°–284° C.; CDC13(TMS), CF$_3$CO$_2$H 7.60 (s, 1H, 7-H), 4.15 (s, 3H, 5-OCH$_3$ or 6-OCH$_3$), 4.03 (s, 3H, 5-OCH$_3$ or 6-OCH$_3$); M+ 256.

EXAMPLE 12

5,6-Dimethoxyquinazoline-1-propionic acid-2,4(1H, 3H)-dione

6-Amino-3,4-dimethoxybenzoic acid (5.5 g, 27.8 m) in glacial acetic acid (100 ml) and acrylic acid (4 ml) was refluxed for 18 hours. Potassium cyanate (5.6 g, 28.4 mM) in H$_2$O (132 ml) was added gradually and stirred for 2 hours at 60° C. After cooling the reaction mixture to 20° C., sodium hydroxide pellets (40 g, 1.0 mole) were added while maintaining the temperature below 60° C. The reaction mixture was then heated at 90° C. for 45 minutes. Upon cooling in an ice bath, the sodium salt of the product precipitated, was filtered, resuspended in H$_2$O (60 ml), acidified (pH 3.0) with concentrated HCl, cooled, and filtered to give the crude product. Trituration with warm isopropanol afforded 2.2 g (25.6%) of the desired product which melted at 226°–228° C.

EXAMPLE 13

5,6-Dimethoxy-8-bromoquinazolin-2,4(1H, 3H)-dione

Following the procedure set forth in Example 11, but using N-bromosuccinimide instead of N-chlorosuccinimide the title compound is obtained in 76.3% yield; mp 264°–266° C.

EXAMPLE 14

5,6-Dimethoxy-8-nitroquinazolin-2,4(1H, 3H)-dione ¾ Hydrate 5,6-Dimethoxyquinazolin-2,4(1H, 3H)-dione (6.1 g, 27.45 mM) was added over a 20 minute period to nitric acid (90%, d=1.5, 18.4 ml) at −9 to −5° C. The reaction mixture was stirred at −7° C. for 1 hour. The temperature was raised to +5° C. for 5 minutes. The reaction mixture was then poured onto ice-H$_2$O (125 ml) and the resulting solid filtered and dried to afford crude product as a rust colored solid. The crude product was triturated with isopropanol (75 ml). An insoluble solid was filtered and dried to afford the title compound as an orangish-brown solid; 0.09 g (1.2%); mp 245°–248° C.; NMR, CF$_3$COOH(TMS), 11.55 (broad s, 1H, N-H), 10.25 (broad s, 1H, N-H), 8.02 (s, 1H, 7-H), 3.90 (s, 6H, 5 and 6-OCH$_3$); M+ 267.

EXAMPLE 15

Ethyl 2,3-dimethoxy-6-nitrobenzoate

Condensation of 2,3-dimethoxy-6-nitrobenzoic acid (1 eg) with (1.5 eg) of triethyl orthoformate gave after isopropanol crystallization an 80% yield of the title compound, mp 120°–122° C.

EXAMPLE 16

Ethyl 3,4-dimethoxy-6-aminobenzoate

Catalytic hydrogenation of ethyl 2,3-dimethoxy-6-nitrobenzoate using 5% Pd/C in EtOH, gave a 90% yield of the title compound, mp 40°–42° C.

EXAMPLE 17

5,6-Dimethoxy-3-methylquinazolin-2,4(1H, 3H)-dione 1/4 Hydrate

A cold solution of ethyl 2,3-dimethoxy-6-aminobenzoate (8.0 g, 35.5 mM) in pyridine (15.4 ml) was added to CH$_3$NCO (3.2 g, 55.9 mM) in pyridine (11.5 ml) at 0° C. The solution was stirred at 0° C. for 30 minutes then at room temperature for 1 hour. The reaction mixture was concentrated to dryness. The resulting brown gummy residue was dissolved in 73 ml of 1N NaOH (4:1, MeOH: H$_2$O, 2.9 g of NaOH pellets in 14.7 ml H$_2$O and 58.3 ml MeOH) and refluxed for 2 hours. The solvent was removed in vacuo to give a light brown solid. This was dissolved in H$_2$O (180 ml) and the pH adjusted to 5 with AcOH. The resulting solid was filtered and dried to afford 6.2 g (73%) of the desired product, mp 247°–250° C.

EXAMPLE 18

3-Benzyl-5,6-dimethoxyquinazolin-2,4(1H, 3H)-dione

Following the procedure employed in Example 17, but using benzylisocyanate instead of methyl isocyanate gives the title compound in 47% yield after isopropanol crystallization; mp 216°–218° C.

EXAMPLE 19

8-Chloro-5,6-dimethoxy-3-methylquinazolin-2,4(1H, 3H)-dione

Following the procedure employed in Example 11, treatment of 5,6-dimethoxy-3-methylquinazolin-2,4(1H, 3H)-dione ¼ hydrate with N-chlorosuccinimide gives the title compound after isopropanol crystallization in 67% yield, mp 224°–227° C.

EXAMPLE 20

2,3-Methylenedioxy-6-nitrobenzoic Acid

Following the procedure employed in Example 7, but using 2,3-methylenedioxy-6-nitrobenzaldehyde instead of 2,3-dimethoxy-6-nitrobenzaldehyde the title compound is obtained in 88% yield, mp 166°–173° C.

EXAMPLE 21

Ethyl 2,3-methylenedioxy-6-nitrobenzoate

Following the procedure employed in Example 15, condensation of 2,3-methylenedioxy 6-nitrobenzoic acid (10 g) with 40 ml of triethyl orthoformate gives the title compound in 67% yield after ethanol crystallization.

EXAMPLE 22

Ethyl 2,3-methylenedioxy-6-aminobenzoate

Catalytic hydrogenation of ethyl 5,6-methylenedioxy-2-nitrobenzoate as in Example 16 using 10% Pd/C gives the title compound in 65% yield after EtOH crystallization, m.p. 96.5°–97.5° C.

EXAMPLE 23

Methyl 2,3-methylenedioxy-6-aminobenzoate

Catalytic hydrogenation of 2,3-methylenedioxy-6-nitrobenzoic acid using 10% Pd/C in MeOH/1N HCl (10:1) gave an 85% yield of the title compound as an oil, whose HCl salt melted at 140°–142° C.

EXAMPLE 24

5,6-Methylenedioxyquinazolin-2,4-dione hemihydrate

The amino methylenedioxy benzoic acid methyl ester (2.0 g, 10.2 mmol) was dissolved in 50 ml glacial acetic acid and potassium cyanate (0.91 g, 11.2 mm) added. The mixture was stirred at 50° C. for 1.5 hours. The solution was brought to pH 10 with approximately 30% NaOH and the resultant suspension was taken to 90° C. for one hour. The mixture was allowed to cool and stood overnight before collecting the solid by frltration and washing with $H_2O$ two times. After drying under vacuum at 90° C. the product was collected in 51% yield as a brown powder, mp 300° C.

EXAMPLE 25

5,6-Methylenedioxy-8-nitroquinazolin-2,4-dione

Following the procedure employed in Example 14, but using 5,6-methylenedioxyquinazolin-2,4(1H, 3H)-dione instead of 5,6-dimethoxyquinazoline-2,4(1H, 3H)-dione, the title compound is obtained, mp 285° C. in 91% yield.

EXAMPLE 26

8-Amino-5,6-methylenedioxyquinazolin-2,4(1H, 3H)-dione

Catalytic hydrogenation of 5,6-methylenedioxy-8-nitroquinazolin-2,4-dione with 10% Pd/C in EtOH affords an 80% yield of the title compound, mp 300° C.

EXAMPLE 27

Ethyl 5-bromo-2,3-methylenedioxy-6-aminobenzoate

Treatment of ethyl 2,3-methylenedioxy-6-aminobenzoate (0.6 g, 2.8 mM) with 1.1 eq of N-bromosuccinimide in $CHCl_3$ (30 ml) for 10 minutes at room temperature affords a product with two spots. After column chromatography over silica gel using $CH_2Cl_2$ as the eluate 0.53 g of the title compound was isolated, mp 81°–83° C.

EXAMPLE 28

Ethyl-5-chloro-2,3-methylenedioxy-6-aminobenzoate

Following the procedure employed in Example 27, treatment of ethyl 5-bromo-2,3-methylenedioxy-6-aminobenzoate with N-chlorosuccinimide instead of N-bromosuccinimide, gave the title compound in 75% yield after silica gel chromatography, mp 77°–78° C.

EXAMPLE 29

8-Chloro-5,6-methylenedioxyquinazolin-2,4(1H, 3H)-dione, Sodium Salt Monohydrate The aminobenzoate prepared in Example 28 (0.800 g, 3.28 mm), was dissolved in glacial acetic acid (25 ml) and potassium cyanate (0.392 g, 4.84 mm) was added. The temperature was taken to 50° C. for two hours, the solution was taken to pH 9 with approximately 30% NaOH. The resultant suspension was cooled to room temperature and the solid collected by filtration. The filter cake was ground to a powder, stirred in EtOH for ½ hour, filtered and the filter cake suspended in $H_2O$ then filtered. The solid collected was dried under vacuum at 82° C. giving a 64% yield of a light yellow powder; mp 300° C.

EXAMPLE 30

Ethyl 5-chloro-2,3-dimethoxy-6-aminobenzoate

Following the procedure employed in Example 27, treatment of ethyl 2,3-dimethoxy-6-aminobenzoate with N-chlorosuccinimide gave a 55% yield of the title compound after EtOH crystallization; mp 60–62%.

EXAMPLE 31

8-Chloro-5,6-dimethoxyquinazoline-1-propionic acid-2,4(1H, 3H)-dione

Following the procedure employed in Example 12, but using ethyl 5-chloro-2,3-dimethoxy-6-aminobenzoate instead of 6-amino-3,4-dimethoxybenzoic acid the title compound is obtained in 20% yield mp 258–260.

EXAMPLE 32

5,6-Dimethoxy-1,3-dimethylquinazolin-2,4(1H, 3H)-dione ¼ Hydrate

Dimethyl sulfate (2.5 ml, 3.33 g, 26.40 mM) was added to 5,6-dimethoxy-3-methylquinazolin-2,4(1H, 3H)-dione (2.0 g, 8.47 mM). The mixture was heated at 80°–85° C. (oil bath temperature) for five minutes. Aqueous KOH (7.9 ml of a 5N solution) was added gradually until the pH of the reaction mixture remained basic. The reaction mixture was cooled and the resulting solid filtered, washed with a small amount of $H_2O$ and dried to afford the title compound as a white solid; 1.74 g (80.6%); mp 136°–139° C.; $CF_3COOH$(TMS) 7.75 (d, 1H, $J_{7,8}$=9.0Hz, 7-H), 7.33 (d, 1H, $J_{8,7}$=9.0Hz, 8-H), 4.28 (s, 3H, 5 or 6-$OCH_3$), 4.07 (s, 3H, 5 or 6-$OCH_3$), 3.80 (s, 3H, 1 or 3-N-$CH_3$), 3.73 (s, 3H, 1 or 3-N-$CH_3$); M+250.

EXAMPLE 33

3-Benzyl-5,6-dimethoxy-1-methylquinazolin-2,4(1H, 3H)-dione

Dimethyl sulfate (1.442 g, 1.08 ml, 11.43 mM) was added to 3-benzyl-5,6-dimethoxyquinazolin-2,4(1H, 3H)-dione (1.20 g, 3.7 mM). The mixture was heated to 80° C. (oil bath temperature) and then heated at 80°–84° C. for five minutes with vigorous stirring. A white solid was present at all times. Aqueous KOH (~15 ml of a 5N aqueous solution) was added dropwise at 80°–90° C. until the pH of the reaction mixture became basic and stayed basic. Addition of the aqueous KOH took ~20 minutes. A white solid was present during the addition. The mixture was cooled in an ice-$H_2O$ bath and the white solid filtered, washed well with $H_2O$ (20 ml) and dried to give 1.00 g crude product. mp 149°–152° C. Recrystallization from isopropanol (50 ml) afforded the title compound as a white solid; 0.80 g (66.1%); mp 153°–155° C. $CDCl_3$(TMS) 7.10–7.80 (m, 6H, 7-H, 10-H, 11-H, 12-H, 13-H, 14-H), 6.82 (d, 1H, $J_{8,7}$=10 Hz, 8-H), 5.25 (s, 2H, 9-H), 3.95 (s, 3H, 5 or 6-$OCH_3$), 3.88 (s, 3H, 5 or 6-$OCH_3$), 3.53 (s, 3H, 1-$CH_3$), M+326.

EXAMPLE 34

5,6-Dimethoxy-3-phenylquinazolin-2,4(1H, 3H)-dione ¼ Hydrate

To phenyl isocyanate (2.26 ml, 2.48 g, 20.8 mM) in pyridine (9.2 ml) at 0° C. was added a cold solution of ethyl 2-amino-5,6-dimethoxybenzoic acid (3.0 g, 13.3 mM) in pyridine (16.7 ml). The solution was stirred at 0° C. for thirty minutes, then kept at room temperature for one hour. The solution was then concentrated to dryness to give a white solid. This was dissolved in 69.9 ml of 1N NaOH (4:1 MeOH-H₂O) and heated at reflux for two hours. The solvent was removed in vacuo and the gummy residue partially dissolved in H₂O (100 ml). The mixture was taken to pH 6 with acetic acid and the resulting white solid filtered, washed well with H₂O (50 ml) and dried to afford crude product as a white solid; 4.13 g, mp 215°-225° C. (softens 190° C.). Recrystallization from isopropanol (250 ml) afforded the title compound as a white solid; 2.65 g (65.8%); mp 241°-243° C. CF₃COOH(TMS) 7.10-7.80 (m, 7H, 7-H, 8-H, 9-H, 10-H, 11-H, 12-H, 13-H), 4.05 (s, 3H, 5 or 6-OCH₃), 10 (s, 3H, 5 or 6-OCH₃). M+298.

EXAMPLE 35

Methyl-3-benzyl-5,6-dimethoxyquinazolin-2,4(1H, 3H)-dione-1-propionate

A solution of 3-benzyl-5,6-dimethoxyquinazolin-2,4(1H, 3H)-dione (0.59 g, 1.8 mM) in methyl acrylate (5.9 ml, 5.64 g, 65.5 mM), Triton B (1.56 ml), MeOH (3.7 ml) and CHCl₃ (9.6 ml) was heated at reflux for sixteen hours. Additional methyl acrylate (6.0 ml, 5.74 g, 66.6 mM) and Triton B (1.56 ml) was added and the reaction mixture was heated at reflux for an additional sixteen hours. The reaction mixture was concentrated in vacuo at 65° C. to give a white solid. The solid was treated with H₂O (10 ml) and the mixture extracted with CH₂Cl₂ (3×30 ml). The CH₂Cl₂ extract was dried (MgSO₄), filtered, and the solvent removed in vacuo to give a yellow semi-solid, 0.76 g. Trituration with ether (50 ml), filtration, and drying gave 0.62 g of an off-white solid. Recrystallization from isopropanol (10 ml), filtration and drying afforded the title compound as a white solid; 0.23 g (31.9%); mp 101°-103° C. CDCl₃(TMS) 7.10-7.70 (m, 6H, 7-H, 10-H, 11-H, 12-H, 13-H, 14-H), 6.88 (d, 1H, J₈,₇=10 Hz, 8-H), 5.21 (s, 2H, 9-H), 4.38 (t, 2H, J=7.0 Hz, 16-H), 3.93 (s, 3H, 5 or 6-OCH₃), 3.85 (s, 3H, 5 or 6-OCH₃),

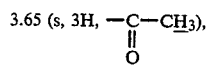
3.65 (s, 3H, —C—CH₃),
       ‖
       O 2.70 (t, 2H, J=7.0Hz, 15-H). M+398.

EXAMPLE 36

Methyl 5,6-dimethoxy-3-methylquinazolin-2,4(1H, 3H)-dione-1-propionate ¼ Hydrate A solution of 5,6-dimethoxy-3-methylquinazolin-2,4(1H, 3H)-dione (0.80 g, 3.39 mM), methyl acrylate (6.7 ml), and Triton B (1.4 ml) in MeOH (5.6 ml) and CHCl₃ (22.4 ml) was heated at reflux for 18 hours. Additional methyl acrylate (6.7 ml) and Triton B (1.4 ml) were added and refluxing continued for 24 more hours. Additional methyl acrylate (6.7 ml) and Triton B (1.4 ml) were added and the mixture was refluxed for an additional 24 hours. The reaction mixture was concentrated to dryness to give a white solid. H₂O (25 ml) was added and the resulting slurry extracted with CH₂Cl₂ (3×20 ml), the extract dried (MgSO₄), filtered and the solvent removed in vacuo to give crude product as an off-white solid. Recrystallization from isopropanol (10 ml) afforded the title compound as a white solid, mp 110°-114° C.; 0.80 g (72.1%); CDCl₃(TMS) 7.25 (d, 1H, J₇,₈=10 Hz, 7-H), 6.92 (d, 1H, J₈,₇=10.0 Hz, 8-H), 4.40 (t, 2H, J=7.0 Hz, 10-H), 3.95 (s, 3H, 5 or 6-OCH₃), 3.90 (s, 3H, 5 or 6-OCH₃),

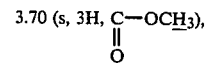
3.70 (s, 3H, C—OCH₃),
       ‖
       O 3.43 (s, 3H, 3-N-CH₃), 2.73 (t, 2H, J=7.0Hz, 9-H); M+322.

EXAMPLE 37

5,6-Dimethoxy-3-(3-methoxyphenyl)quinazolin-2,4(1H, 3H)-dione

To 3-methoxyphenyl isocyanate (2.8 ml, 3.13 g, 20.97 mM) in pyridine (4.7 ml) at 0° C. was added a cold solution of 2-amino-5,6-dimethoxybenzoic acid ethyl ether (3.0 g, 13.32 mM) in pyridine (7.1 ml). The solution was stirred at 0° C. for thirty minutes, then at room temperature for one hour. The solution was then concentrated to dryness to give a red solid. This was dissolved in 30.0 ml of 1N NaOH (4:1, MeOH:H₂O) and heated at reflux for two hours. The solvent was removed in vacuo and the resulting gummy red solid partially dissolved in H₂O (20 ml). The mixture was taken to pH 5 with acetic acid and the resulting solid filtered and dried to afford crude product as a pink solid. The crude product was triturated with isopropanol (75 ml). The insoluble solid was filtered and dried to afford the title compound as a white solid, mp 201°-203° C. (yield 1.94 g, 44%), CF₃COOH(TMS), 10.27-10.50 (broad s, 1H, 1-N-H), 6.97-7.77 (m, 6H, 7-H, 8-H, 9-H, 10-H, 11-H, 13-H), 4.12 (s, 3H, 5, 6 or aryl-OCH₃), 4.07 (s, 3H, 5, 6 or 12-OCH₃), 4.02 (s, 3H, 5, 6 or aryl-OCH₃); M+328.

EXAMPLE 38

3-Ethyl-5,6-dimethoxyquinazolin-2,4(1H, 3H)-dione

To ethyl isocyanate (1.65 ml, 1.48 g, 20.8 mM) in pyridine (9.2 ml) at 0° C. was added a cold solution of 2-amino-5,6-dimethoxybenzoic acid ethyl ester (3.0 g, 20.8 mM) in pyridine (16.7 ml). The solution was stirred at 0° C. for thirty minutes, then kept at room temperature for one hour. During this time, a precipitate formed. The mixture was concentrated to dryness to give an off-white solid. This was dissolved in 69.9 ml of 1N NaOH (4:1 MeOH-H₂O) and heated at reflux for two hours. The solvent was removed in vacuo and the residue dissolved in H₂O (150 ml). The mixture was taken to pH 6 with acetic acid and the resulting white solid filtered, washed with H₂O (50 ml), and dried to give crude product as a white solid; 3.12 g; mp 208°-211° C. Recrystallization from isopropanol (100 ml) and drying afforded the title compound as a white solid; 2.09 g; mp 212°-214° C., total yield 80.5%, CF₃COOH(TMS), 7.60 (d, 1H, J₇,₈=9.0 Hz, 7-H), 7.13 (d, 1H, J₈,₇=9.0 Hz, 8-H), 4.20 (9, 2H, J=6.0 Hz, 9-H), 4.19 (s, 3H, 5 or 6-OCH₃), 4.05 (s, 3H, 5 or 6-OCH₃), 1.40 (t, 3H, J=6.0 Hz, 10-H). M+250.

EXAMPLE 39

Methyl 5,6-dimethoxy-3-(3-methoxyphenyl)quinazolin-2,4(1H, 3H)-dione-1-propionate Hemihydrate A solution of 5,6-dimethoxy-3-(3-methoxyphenyl)-quinazolin-2,4(1H, 3H)-dione (1.5 g, 4.57 mM), methyl acrylate (9.0 ml) and Triton B (1.9 ml) in MeOH (7.5 ml) and CHCl$_3$ (30.2 ml) was heated at reflux for 18 hours. Additional methyl acrylate (9.0 ml) and Triton B (1.9 ml) were added and refluxing continued for 18 hours. The reaction mixture was concentrated to dryness in vacuo to give a pink semisolid. Water (30 ml) was added and the resulting slurry was extracted with CH$_2$Cl$_2$ (3×50 ml). The CH$_2$Cl$_2$ extract was dried (MgSO$_4$), filtered, and the solvent removed in vacuo to give a 53% yield of the title compound as a white solid, mp 164°–166° C.; CDCl$_3$(TMS), 6.70–7.43 (m, 6H, 7-H, 8-H, 11-H, 12-H, 13-H, 15-H), 4.42 (t, 2H, J=7.0 Hz, 10-H), 3.90 (s, 3H, 5, 6 or 14-OCH$_3$), 3.88 (s, 3H, 5, 6 or 14-OCH$_3$), 3.78 (s, 3H, 5, 6 or 14-OCH$_3$),

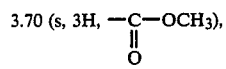

3.70 (s, 3H, —C(=O)—OCH$_3$), 2.77 (t, 2H, J=7.0 Hz, 9-H); M+414.

EXAMPLE 40

3-(4-Chlorophenyl)-5,6-dimethoxyquinazolin-2,4(1H, 3H)-dione ¼ Hydrate

To p-chlorophenyl isocyanate (2.7 ml, 3.22 g, 20.97 mM) in pyridine (4.7 ml) at 0° C. was added a cold solution of 2-amino-5,6-dimethoxybenzoic acid ethyl ester (3.0 g, 13.32 mM) in pyridine (7.1 ml). The reaction mixture solidified shortly after the addition of the ester. The reaction mixture was allowed to go to room temperature but remained a solid. More pyridine (15 ml) was added and the pink slurry stirred at room temperature for three hours. The solvent was removed in vacuo to give a pink solid. The solid was triturated with 300 ml of 1N NaOH (4:1, MeOH:H$_2$O) was added and the solution was heated at reflux for 2 hours. The solvent was removed in vacuo and the reddish solid partially dissolved in H$_2$O (25 ml). The pH was adjusted to 5 with acetic acid and the resulting solid filtered, washed with H$_2$O (~75 ml) and dried to give crude product as a pink solid. The crude product was triturated with MeOH. The insoluble solid was filtered to afford the title compound as a white solid; 2.66 g; mp 269°–273° C., CF$_3$COOH(TMS), 7.10–7.77 (m, 6H, 7-H, 8-H, 9-H, 10-H, 12-H 13-H), 4.12 (s, 3H, 5 or 6-OCH$_3$), 4.07 (s, 3H, 5 or 6-OCH$_3$); M+332.

EXAMPLE 41

3-n-Butyl-5,6-dimethoxyquinazolin-2,4-(1H, 3H)-dione Hemihydrate

To n-butyl isocyanate (2.06 g, 2.34 ml, 20.8 mM) in pyridine (9.2 ml) at 0° C. was added a cold solution of 2-amino-5,6-dimethoxybenzoic acid ethyl ester (3.0 g, 13.3 mM) in pyridine (16.7 ml). The solution was stirred at 0° C. for thirty minutes, then kept at room temperature for one hour. The mixture was concentrated to dryness to give an off-white solid. This was dissolved in 69.9 ml of 1N NaOH (4:1 MeOH-H$_2$O) and heated at reflux for 2 hours. The solvent was removed in vacuo and the residue dissolved in H$_2$O (150 ml). The mixture was taken to pH 6 with acetic acid and the resulting white solid filtered, washed with H$_2$O (50 ml) and dried to afford the title compound as a white solid; 2.38 g (64.3%); mp 159°–161° C.; CDCl$_3$(TMS) 7.21 (d, 1H, J$_{7,8}$=9.0 Hz, 7-H), 6.82 (d, 1H, J$_{8,7}$=9.0 Hz, 8-H), 4.10 (t, 2H, J$_{9,10}$=7.0 Hz, 9-H), 3.95 (s, 3H, 5 or 6-OCH$_3$), 3.85 (s, 3H, 5 or 6-OCH$_3$), 0.80–2.10 (m, 7H, 10-H, 11-H, 12-H), M+278.

EXAMPLE 42

Methyl 3-(4-chlorophenyl)-5,6-dimethoxyquinazolin-2,4(1H, 3H-dione-1-propionate

A solution of 3-(4-chlorophenyl)-5,6-dimethoxyquinazolin-2,4(1H, 3H)-dione ¼ hydrate (3.75 g, 11.12 mM), methyl acrylate (21.9 ml), Triton B (4.6 ml) in MeOH (18.2 ml) and CHCl$_3$ (73.5 ml) was heated at reflux for 18 hours. Additional methyl acrylate (21.9 ml) and Triton B (4.6 ml) were added and the refluxing was continued for 24 more hours. The reaction mixture was cooled and concentrated in vacuo to give a peach colored semi-solid. Water (75 ml) was added and the slurry extracted with CH$_2$Cl$_2$ (175 ml), dried (MgSO$_4$), filtered, and the solvent removed in vacuo to give the crude product as an off-white solid. The crude product was triturated with MeOH (75 ml) to give the title compound as a white solid, 1.46 g; mp 167°–170° C., total yield 59.4%, CDCl$_3$(TMS) 6.87–7.58 (m, 6H, 7-H, 8-H, 11-H, 12-H, 14-H, 15-H), 4.42 (t, 2H, J=7.0 Hz, 10-H), 3.92 (s, 6H, 5 and 6-OCH$_3$),

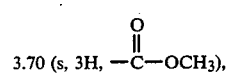

3.70 (s, 3H, —C(=O)—OCH$_3$), 2.77 (t, 2H, J=7.0 Hz, 9-H); M+418.

The following compounds were prepared according to the methods described in Examples 32–42 using appropriately substituted starting materials.

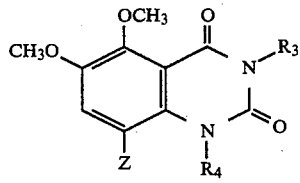

| Example | mp/°C. | % Yield | Z | R$_4$ | R$_3$ |
|---|---|---|---|---|---|
| 43 | 136–139 | 80.6 | H | CH$_3$ | CH$_3$ |
| 44 | 153–155 | 66.1 | H | CH$_3$ | —CH$_2$φ |
| 45 | 241–243 | 65.8 | H | H | φ |
| 46 | 101–103 | 31.9 | H | —CH$_2$CH$_2$CO$_2$CH$_3$ | CH$_2$φ |

-continued
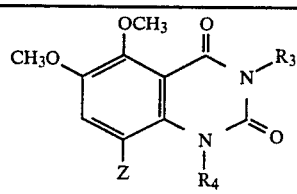
| Example | mp/°C. | % Yield | Z | R₄ | R₃ |
|---------|--------|---------|---|-----|-----|
| 47 | 110–114 | 72.1 | H | —CH₂CH₂CO₂CH₃ | CH₃ |
| 48 | 191–194 | 44.0 | H | H | 3-methoxyphenyl |
| 49 | 208–211 | 80.5 | H | H | —CH₂CH₃ |
| 50 | 165–167 | 53.4 | H | —CH₂CH₂CO₂CH₃ | 3-methoxyphenyl |
| 51 | 262–265 | 100.0 | H | H | 4-chlorophenyl |
| 52 | 159–161 | 64.5 | H | H | —CH₂CH₂CH₃ |
| 53 | 169–172 | 59.4 | H | —CH₂CH₂CO₂CH₃ | 4-chlorophenyl |
| 54 | 135–137 | 75.0 | H | H | —CH₂CH₂CH₂—N(morpholino) |
| 55 | 165–167 | 84.0 | H | H | —N(piperidino) |
| 56 | 139–144 | 30.0 | H | H | —N(piperidino) |
| 57 | 197–199 | 60.0 | Cl | H | —N(piperidino) |
| 58 | 197–199 | 75.0 | Cl | H | —N(piperidino) |
| 59 | 160–162.5 | 7.0 | H | H | —CH₂CH₂CH₂—OH |
| 60 | 82–84 | 18.0 | H | H | —CH(CH₂CH₃)(CH₂OH) |

-continued

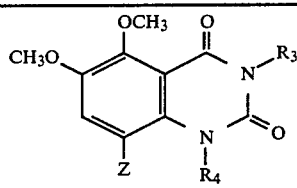

| Example | mp/°C. | % Yield | Z | R4 | R3 |
|---|---|---|---|---|---|
| 61 | 149–151 | 20.0 | Cl | H | —CH(CH2CH3)(CH2OH) |

EXAMPLE 62

3-(2-Chloroethyl)-5,6-dimethoxyquinazolin-2,4(1H, 3H)-dione

A mixture of 5,6-dimethoxy-3-hydroxyethylquinazolin-2,4-dione (2.0 g, 7.51 mM) and thionyl chloride (0.76 ml, 10.45 mM) in CHCl3 (20 ml) was heated at reflux for 4 hours under nitrogen with vigorous mechanical stirring. Trituration of the solid reaction mixture followed by drying afforded crude product as an off-white solid. The crude product was recrystallized from MeOH (100 ml) and dried to afford the title compound as a white solid; 0.86; (A); mp 118°–120° C.

EXAMPLE 63

3-Hydroxyethylaminoethyl-5,6-dimethoxyquinazolin-2,4(1H, 3H)-dione

A mixture of ethyl 2-carbethoxy-3,4-dimethoxyphenyl carbamate (2.0 g, 6.73 mM) and 2-[2-aminoethylamino]ethanol (1.22 ml, 1.26 g, 12.11 mM) was heated at 160°–170° C. with stirring for 45 minutes. The reaction mixture was concentrated under vacuum and the semi-solid residue was triturated with isopropanol (~75 ml) and dried to give the crude product as a tan solid. Recrystallization from isopropanol (50 ml) afforded the title compound as a white solid, 0.63 g (30.3%), mp 142–145° C.

EXAMPLE 64

3-(2-Hydroxyethyl)-5,6-dimethoxyquinazolin-2,4-(1H, 3H)-dione

A mixture of ethyl 2-carbethoxy-3,4-dimethoxyphenyl carbamate (2.1 g, 7.2 mM) and 2-aminoethanol (0.78 ml, 0.792 g, 12.96 mM) was stirred and heated at 160°–170° C. for 30 minutes. The semi-solid residue was concentrated in vacuo and the residue was triturated with isopropanol (30 ml). The insoluble material was filtered and dried to afford the title compound as an off-white solid; 1.17 g (60.9%, mp 222°–224° C.

EXAMPLE 65

5,6-Dimethoxy-3,4(1H, 3H)quinazolindione-1-propionitrile

A solution of 5,6-dimethoxy-2,4(1H, 3H)-quinazolindione (10 g) in chloroform (100 ml), methanol (100 ml) and acrylonitrile was treated with 20 ml of Triton B (40% in methanol (100 ml). The solution was refluxed with stirring for 24 hours, cooled to room temperature and the solvent is removed by evaporation in vacuo. The resulting residue was chromatographed on silica gel using CH2Cl2 as the eluent to give purified 5,6-dimethoxy-2,4(1H, 3H)-quinazolinone-1-propionitrile.

The cardiotonic activity of the substituted quinazolinediones is determined according to the following general procedure:

Adult mongrel dogs are anesthetized with sodium pentobarbital (45 mg/kg, i.p.) and artificially respired. Arterial pressure (MAP) is recorded via a femoral artery and the pressure pulse is used to trigger a cardiotachometer for heart rate (HR). Left ventricular pressure is measured with a Millar catheter and dP/dt$_{max}$ is derived. A right thoracotomy is performed and cardiac output (CO) is determined by measuring ascending aortic blood flow with an electromagnetic flow probe. Myocardial contractile force (CF) is measured with a Walton Brode strain gauge sutured to the right ventricle. A lead II EKG is also recorded. A standard dose of dopamine is administered to determine myocardial responsiveness. Compounds are administered by i.v. infusion and dose-related effects of the test compound on MAP, HR, dP/dt$_{max}$, CF and CO are expressed as a percent change from pretreatment control.

The cardiotonic activity of some representative compounds of this invention is tabulated below:

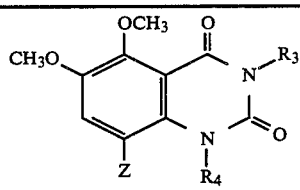

| | | | Activity (% Δ from control) | | | | | |
|---|---|---|---|---|---|---|---|---|
| R4 | R3 | Z | MAP | HR | dp/dt | CF | n | Cum. Dose (mg/kg) |
| H | H | H | −9 | 16 | 61 | 89 | 2 | 1.75 |
| H | H | Cl | −14 | 24 | 65 | 148 | 4 | 0.875 |

-continued

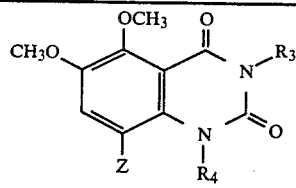

| R4 | R3 | Z | MAP | HR | dp/dt | CF | n | Cum. Dose (mg/kg) |
|---|---|---|---|---|---|---|---|---|
| H | H | Br | −10 | 10 | 21 | 84 | 2 | 0.875 |
| *H | H | Cl | 4 | 5 | 22 | 28 | 1 | 1.875 |
| H | CH$_3$ | H | −4 | 11 | 104 | 104 | 1 | 0.875 |
| H | —CH$_2$φ | H | 3 | 9 | 25 | 24 | 1 | 1.875 |
| H | φOCH$_3$—p | H | −2 | 11 | 33 | 34 | 1 | 1.875 |
| H | —φCl—p | H | 3 | 1 | 10 | 14 | 1 | 1.875 |
| H | —CH$_2$CH$_3$ | H | −20 | 18 | 59 | 100 | 1 | 0.875 |
| H | n-butyl | H | −4 | 49 | 70 | 83 | 1 | 1.875 |
| CH$_3$ | —CH$_2$φ | H | 3 | 6 | 35 | 20 | 1 | 1.875 |
| —(CH$_2$)$_2$CO$_2$Me | CH$_3$ | H | −3 | 4 | 6 | 27 | 1 | 1.875 |
| —(CH$_2$)$_2$CO$_2$Me | —CH$_2$φ | H | −12 | 17 | 28 | 24 | 1 | 1.875 |
| H | H | NO$_2$ | 1 | 10 | 39 | 74 | 1 | 1.875 |
| H | CH$_2$CH$_2$OH | H | −4 | 24 | 57 | 59 | 1 | 1.875 |
| C$_2$H$_5$ | φ-Cl—p | H | 7 | 6 | 9 | 8 | 1 | 1.875 |
| H | CH$_2$CH$_2$NHCH$_2$CH$_2$OH | H | 4 | 9 | 19 | 17 | 1 | 1.875 |
| H | CH$_2$CH$_2$Cl | H | 0 | 2 | 12 | 16 | 1 | 1.875 |

MAP = Mean Article Pressure;
HR = Heart Rate;
dp/dt = Rate of Change of Pressure with Time;
CF = Contractile Force;
n = Number of animals
*wherein R$_1$ and R$_2$ taken together are methylenedioxy.

We claim:

1. A compound of the formula

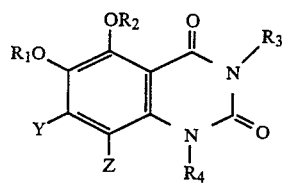

wherein R$_1$ and R$_2$ are the same or different substituents and are hydrogen, lower alkyl having 1-5 carbon atoms or —CH$_2$— when taken together; Y and Z are the same or different and are hydrogen, nitro, amino, acetamido, alkylamino wherein the alkyl group 1-5 carbon atoms, alkyl wherein the alkyl group has 1-5 carbon atoms, cycloalkylamino wherein the cycloalkyl group has 4-8 carbon atoms, and cycloalkyldiamino wherein the cycloalkyl group has 4-8 carbon atoms, carboxy, carboalkoxy wherein the alkoxy group has 1-5 carbon atoms, cyano, methanesulfonyl, carboxamide, and halo; R$_3$ is hydrogen, alkyl wherein the alkyl group has 1-5 carbon atoms, hydroxyalkyl wherein the alkyl group has 1-5 carbon atoms, haloalkyl wherein he alkyl group has 1-5 carbon atoms, amino, dialkylamino wherein the alkyl group has 1-5 carbon atoms, dialkylamino alkyl wherein the alkyl group has 1-5 carbon atoms, cycloalkylamino and cycloalkylaminoalkyl wherein the alkyl group has 1-5 carbon atoms and the cycloalkyl group has 5-6 carbon atoms, phenyl, substituted phenyl wherein the substituent is halo, lower alkoxy, alkyl having 1-5 carbon atoms; alkylphenyl wherein the alkyl group has 1-5 carbon atoms; substituted alkylphenyl wherein the substituent is nitro, amino, alkylamino having 1-5 carbon atoms, cycloalkylamino and cyclodialkylamino wherein the cycloalkyl group has 4-8 carbon atoms, carboxy, carboalkoxy wherein the alkoxy group has 1-5 carbon atoms, mono- and dihydroxy, cyano, methanesulfonyl, carboxamide or halo; R$_4$ is hydrogen, lower alkyl wherein the alkyl group has 1-5 carbon atoms, carboalkoxy and R$_5$CH$_2$CH$_2$X wherein R$_5$ is hydrogen or lower alkyl; X is carboxy, carboalkoxy wherein the alkoxy group has 1-3 carbon atoms, cyano, carboxamido, methanesulfonyl, formyl, benzoyl and substituted benzoyl and the pharmaceutically acceptable salts thereof; provided that when R$_3$ is amino or alkylamino wherein the alkyl group has 1-5 carbon atoms, Y and Z are not simultaneously hydrogen.

2. The compound of claim 1 wherein R$_4$ is hydrogen, R$_3$ is hydrogen, R$_1$ and R$_2$ are lower alkyl and Z is halo.

3. The compound of claim 1 wherein R$_3$ and R$_4$ are hydrogen, R$_1$ and R$_2$ are methyl and Z is chloro.

4. The compound of claim 1 wherein R$_1$, R$_2$ and R$_3$ are methyl, R$_4$ is hydrogen, Y is hydrogen and Z is hydrogen chloro.

5. A compound of claim 1 selected from the group consisting of 5,6-dimethoxyquinazolin-2,4(1H, 3H)-dione; 5,6-dimethoxy-8-chloroquinazolin-2,4(1H, 3H)-dione; 5,6-dimethoxy-8-bromoquinazolin-2,4(1H, 3H)-dione; and 5,6-dimethoxy-8-nitroquinazolin-2,4(1H, 3H)-dione.

6. A compound of claim 1 selected from the group consisting of 5,6-dimethoxy-3-methylquinazolin-2,4(1H, 3H)-dione; 3-benzyl-5,6-dimethoxyquinazolin-2,4(1H, 3H)-dione and 8-chloro-5,6-dimethoxy-3-methyl-quinazolin-2,4(1H, 3H)-dione.

7. A compound of claim 1 selected from the group consisting of 5,6-methylenedioxyquinazolin-2,4(1H, 3H)-dione; 5,6-methylenedioxy-8-nitroquinazolin-2,4(1H, 3H)-dione; 8-amino-5,6-methylenedioxy-2,4(1H, 3H)-dione and 8-chloro-5,6-methylenedioxyquinazolin-2,4(1H, 3H)-dione.

8. A compound of claim 1 selected from the group consisting of 8-chloro-5,6-dimethoxyquinazolin-1-propionic acid-2,4(1H, 3H)-dione; methyl-3-benzyl-5,6-dimethoxyquinazolin-2,4(1H, 3H)-dione-1-propionate; methyl 5,6-dimethoxy-3-(3-methoxyphenyl) quinazolin-2,4(1H, 3H)-dione-1-propionate; methyl 3-(4-chlorophenyl)-5,6-dimethoxyquinazolin-2,4(1H, 3H)-dione-1-propionate and methyl 5,6-dimethoxy-3-methylquinazolin-2,4(1H, 3H)-dione-1-propionate.

* * * * *

UNITED STATES PATENT AND TRADEMARK OFFICE
CERTIFICATE OF CORRECTION

PATENT NO. : 4,639,518

DATED : January 27, 1987

INVENTOR(S) : Victor T. Bandurco et al.

It is certified that error appears in the above-identified patent and that said Letters Patent is hereby corrected as shown below:

Column 22, Claim 4, line 51, "hydrogen chloro" should read --hydrogen or chloro--.

Signed and Sealed this

First Day of December, 1987

Attest:

DONALD J. QUIGG

*Attesting Officer*   *Commissioner of Patents and Trademarks*